United States Patent

Sisko

[11] Patent Number: 5,917,043
[45] Date of Patent: Jun. 29, 1999

[54] 4-ARYL-5-PYRIMIDINE IMIAZOLE SUBSTITUTED COMPOUNDS

[75] Inventor: Joseph Sisko, Hatfield, Pa.

[73] Assignee: SmithKline Beecham Corporation, Philadelphia, Pa.

[21] Appl. No.: 08/771,320

[22] Filed: Dec. 20, 1996

Related U.S. Application Data

[60] Provisional application No. 60/009,098, Dec. 22, 1995.

[51] Int. Cl.[6] .................. C07D 239/02; A61K 31/605
[52] U.S. Cl. .................. 544/332; 514/275; 544/333; 546/210; 548/333.5
[58] Field of Search .................. 544/333, 332; 548/333.5; 514/275; 546/210

[56] References Cited

U.S. PATENT DOCUMENTS

| | | | |
|---|---|---|---|
| 3,707,475 | 12/1972 | Lombardino | 514/399 X |
| 3,772,441 | 11/1973 | Lombardino | 424/273 |
| 3,929,807 | 12/1975 | Fitzi | 514/399 X |
| 3,940,486 | 2/1976 | Fitzi | 424/263 |
| 4,058,614 | 11/1977 | Baldwin | 424/263 |
| 4,199,592 | 4/1980 | Cherkofsky | 424/273 R |
| 4,447,431 | 5/1984 | Sallmann | 424/246 |
| 4,503,065 | 3/1985 | Wilkerson | 514/396 |
| 4,565,875 | 1/1986 | Cavender | 548/335.1 |
| 4,686,231 | 8/1987 | Bender et al. | 514/333 |
| 4,822,805 | 4/1989 | Tasasugi et al. | 514/341 |
| 5,096,915 | 3/1992 | Parsons et al. | 514/398 |
| 5,234,917 | 8/1993 | Finkelstein et al. | 514/397 |
| 5,312,828 | 5/1994 | Finkelstein et al. | 514/381 |
| 5,593,991 | 1/1997 | Adams et al. | 514/235.2 |
| 5,593,992 | 1/1997 | Adams et al. | 514/235.8 |
| 5,658,903 | 8/1997 | Adams et al. | 514/235.8 |
| 5,663,334 | 9/1997 | Sheldrake et al. | 544/122 |
| 5,670,527 | 9/1997 | Adams et al. | 514/341 |

FOREIGN PATENT DOCUMENTS

| | | |
|---|---|---|
| WO92/10190 | 6/1992 | WIPO . |
| WO92/10498 | 6/1992 | WIPO . |
| WO95/02591 | 1/1995 | WIPO . |
| WO 95/09847 | 4/1995 | WIPO . |
| WO 95/09851 | 4/1995 | WIPO . |
| WO 95/09852 | 4/1995 | WIPO . |
| WO 95/09853 | 4/1995 | WIPO . |
| WO 96/21654 | 7/1996 | WIPO . |

OTHER PUBLICATIONS

Dinarello, Rev.Infect.Disease, 6, p. 51 (1984).
Dinarello et al, J.Clin.Immun., 5(5), pp. 287–297 (1985).
R.P.Soni, Aust.J.Chem., 35, pp. 1493–1496 (1982).
Poli et al., Proc.Nat'l Acad.Sci., 87, pp. 782–784 (1990).
VanLeusen et al., J.O.C., 42, p. 1153 (1977).
Minato et al., Tetrahedron Letters, 22, p. 5319 (1981).
Pridgen, J.Org. Chem., 47, p. 4319 (1982).
Echavarren et al, J. Amer.Chem.Soc., 109, p. 5478 (1978).
Fischer et al., Rec.Trav.Chim.Pays.Bas., 84, p. 439 (1965).
Alves et al, Tetrahedron Letters, 29, 2135 (1988).
Ishikura et al, Chem.Pharm.Bull., 11, p. 4755 (1985).
Thompson, W.J., et al., J.Org.Chem., 49, p. 5237 (1984).
Garigipati, R., Tetrahedron Letters, 31, p. 190 (1989).
Engel & Steglich, Liebigs Ann. Chem., 1916 (1978).

*Primary Examiner*—Floyd D. Higel
*Attorney, Agent, or Firm*—Dara L. Dinner; Stephen Venetianer

[57] ABSTRACT

The present invention relates to a novel method for synthesizing imidazole derivatives having 4-aryl, 5-pyrimidine heterocyclic rings using a novel cycloaddition reaction.

6 Claims, No Drawings

4-ARYL-5-PYRIMIDINE IMIAZOLE SUBSTITUTED COMPOUNDS

This application claims the benefit of provisional application Ser. No. 60/009,098 filed Dec. 22, 1995.

FIELD OF THE INVENTION

The present invention relates to a novel method for synthesizing imidazole derivatives having 4-aryl, 5-pyrimidine heterocyclic rings.

BACKGROUND OF THE INVENTION

The present invention describes a novel, and general method to prepare 5-pyrimidinyl substituted imidazoles. Previous syntheses of is class of molecules utilized the van Leusen reaction (van Leusen, A.M., et. al. *J. Org. Chem.* 1977, 42, 1153), which involves the cycloaddition of an imine and a tosylisonitrile. Difficulties in preparing the aldehyde precursors to the desired imines limited the scope of this approach. In Adams et al., WO 95/02591 an improvement on the cycloaddition reaction is shown for similar compounds. However addition of a pyrimidine rig in an environmentally favourable and commercially feasible manner is still needed. The present invention employs a novel method of cycloaddition of a tosylisonitrile with an α-ketoaldimine to produce a 5-keto imidazole derivative. The 5-keto group serves as an excellent precursor for addition of the optionally substituted pyrimidine ring.

SUMMARY OF THE INVENTION

The present invention is to a process of making compounds of Formula (I),

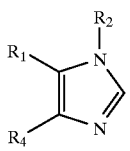

(I)

wherein
$R_1$ is an optionally substituted pyrimidin-4-yl ring;
$R_4$ is an optionally substituted phenyl, naphth-1-yl or naphth-2-yl, or heteroaryl ring;
m is 0, or the integer 1 or 2;
m' is an integer having a value of 1 or 2,
$R_2$ is -$(CR_{10}R_{20})_{n'}$ ($OR_9$, heterocyclyl, heterocyclyl$C_{1-10}$ alkyl, $C_{1-10}$alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$ alkyl, $C_{5-7}$ cycloalkenyl, $C_{5-7}$cycloalkenyl-$C_{1-10}$-alkyl, aryl, aryl$C_{1-10}$ alkyl, heteroaryl, heteroaryl-$C_{1-10}$-alkyl, $(CR_{10}R_{20})_nOR_{11}$, $(CR_{10}R_{20})_nS(O))_mR_{18}$, $(CR_{10}R_{20})_nNHS(O)_2R_{18}$, $(CR_{10}R_{20})_nNR_{13}R_{14}$, $(CR_{10}R_{20})_nNO_2$, $(CR_{10}R_{20})_nCN$, $(CR_{10}R_{20})_{n'}SO_2R_{18}$, $(CR_{10}R_{20})_nS(O)_{m'}NR_{13}R_{14}$, $(CR_{10}R_{20})_nC(Z)R_{11}$, $(CR_{10}R_{20})_nOC(Z)R_{11}$, $(CR_{10}R_{20})_nC(Z)OR_{11}$, $(CR_{10}R_{20})_nC(Z)NR_{13}R_{14}$, $(CR_{10}R_{20})_nC(Z)NR_{11}$ $_{OR9}$, $(CR_{10}R_{20})_nNR_{10}C(Z)R_{11}$, $(CR_{10R20})_nNR_{10}C(Z)NR_{13}R_{14}$, $(CR_{10}R_{20})_nN(OR_6)C(Z)NR_{13}R_{14}$, $(CR_{10}R_{20})_nN(OR_6)C(Z)R_{11}$, $(CR_{10}R_{20})_nC(=NOR_6)R_{11}$, $(CR_{10}R_{20})_nNR_{10}C(=NR_{19})NR_{13}R_{14}$, $(CR_{10}R_{20})_nOC(Z)NR_{13}R_{14}$, $(CR_{10}R_{20})_nNR_{10}C(Z)NR_{13}R_{14}$, $(CR_{10}R_{20})_nNR_{10}C(Z)OR_{10}$, 5-($R_{18}$)-1,2,4-oxadizaol-3-yl or 4-($R_{12}$)-5-($R_{18}R_{19}$)-4,5-dihydro-1,2,4-oxadiazol-3-yl; wherein the aryl, arylalkyl, heteroaryl, heteroamyl alkyl, heterocyclic and heterocyclic alkyl groups may be optionally substituted;

n is an integer having a value of 1 to 10;
n' is 0, or an integer having a value of 1 to 10;
Z is oxygen or sulfur;
$R_3$ is heterocyclyl, heterocyclyl$C_{1-10}$ alkyl or $R_8$;
$R_6$ is hydrogen, a pharmaceutically acceptable cation, $C_{1-10}$ alkyl, $C_{3-7}$ cycloalyl, aryl, aryl$C_{1-4}$ alkyl, heteroaryl, heteroarylalkyl, heterocyclyl, aryl, or $C_{1-10}$ alkanoyl;
$R_8$ is $C_{1-10}$ alkyl, halo-substituted $C_{1-10}$alkyl, $C_{2-10}$alkenyl, $C_{2-10}$ alkynyl, $C_{2-10}C_{3-7}$ cycloalkyl, $C_{5-7}$ cycloalkenyl, aryl, aryl$C_{1-10}$ alkyl, heteroaryl, heteroaryl$C_{1-10}$ alkyl, $(CR_{10}R_{20}D)_nOR_{11}$, $(CR_{10}R_{20})_nS(O)_mR_{18}$, $(CR_{10}R_{20})_nNHS(O)_2R_{18}$, $(CR_{10}R_{20})_nNR_{13}R_{14}$; wherein the aryl, arylalkyl, heteroaryl, heteroaryl alkyl may be optionally substituted;
$R_9$ is hydrogen, —$C(Z)R_{11}$ or optionally substituted $C_{1-10}$ alkyl, $S(O)_2R_{18}$, optionally substituted aryl or optionally substituted aryl-$C_{1-4}$ alkyl;
$R_{10}$ and $R_{20}$ is each independently selected from hydrogen or $C_{1-4}$ alkyl;
$R_{11}$ is hydrogen, $C_{1-10}$ alkyl, $C_{3-7}$ cycloalkyl, heterocyclyl, heterocyclyl $C_{1-10}$alkyl, aryl, aryl$C_{1-10}$ alkyl, heteroaryl or heteroaryl$C_{1-10}$ alkyl;
$R_{12}$ is hydrogen or $R_{16}$;
$R_{13}$ and $R_{14}$ is each independently selected from hydrogen or optionally substituted $C_{1-4}$ alkyl, optionally substituted aryl or optionally substituted aryl-$C_{1-4}$ alkyl, or together with the nitrogen to which they are attached form a heterocyclic ring of 5 to 7 members which ring optionally contains an additional heteroatom selected from oxygen, sulfur or $NR_9$;
$R_{16}$ is $C_{1-4}$ alkyl, halo-substituted-$C_{1-4}$ alkyl, or $C_{3-7}$ cycloalkyl;
$R_{18}$ is $C_{1-10}$ alkyl, $C_{3-7}$ cycloalkyl, heterocyclyl, aryl, arylalkyl, heterocyclyl, heterocyclyl-$C_{1-10}$alkyl, heteroaryl or heteroarylalkyl; and
$R_{19}$ is hydrogen, cyano, $C_{1-4}$ alkyl, $C_{3-7}$ cycloalkyl or aryl;
which process comprises:

a) reacting a compound of formula (II), as defined below

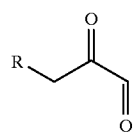

(II)

wherein R is the optional substituent on the pyrimidinyl ($R_1$) moiety in Formula (I), or is hydrogen, an optionally substituted alkyl or an optionally substituted aryl, with a compound of the Formula $R_2NH_2$ (III), wherein $R_2$ is as defined for Formula (I), to yield a compound of Formula (IV)

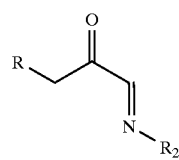

(IV)

wherein R and $R_2$ are as defined above; and b) reacting a compound of Formula (IV) with a compound of Formula (V) and a suitable base,

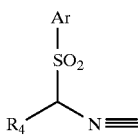
(V)

wherein Ar is an optionally substituted aryl; and R₄ is as defined for Formula (I); to yield a compound of Formula (VI)

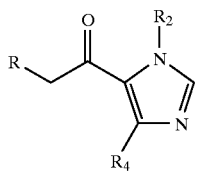
(VI)

wherein R, R₂ and R₄ are as defined above; and
c) reacting a compound of Formula (VI) with a compound of Formula VII

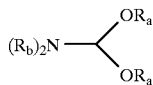
(VII)

wherein $R_a$ is alkyl, aryl, heteroaryl, cycloalkyl, cycloalkenyl, arylalkyl, heteroarylalkyl, heterocylic, or heterocyclicalkyl group all of which may be optionally substituted; and $R_b$ is alkyl, aryl, heteroaryl, cycloalkyl, cycloalkenyl, arylalkyl, heteroarylalkyl, heterocylic, or heterocyclicalkyl group all of which may be optionally substituted; to yield a compound of Formula (VIII)

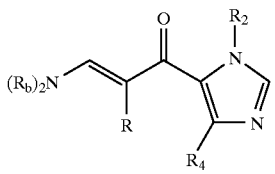
(VIII)

wherein $R_b$ is as defined above for Formula (VII), R is as defined above, and R₂ and R₄ are defined as for Formula (I);
d) reacting a compound of Formula (VEII) with a compound of Formula (IX)

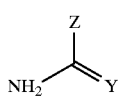
IX wherein
Z is N(R$^d$)₂, SR$^e$, OR$^e$, or R$^d$.
R$^d$ is independently hydrogen, alkyl, aryl, heteroaryl, cycloalkyl, cycloalkenyl, arylalkyl, heteroarylalkyl, heterocylic, or heterocyclicalkyl;
R$^e$ is alkyl, aryl, heteroaryl, cycloalkyl, cycloalkenyl, arylalkyl, heteroarylalkyl, heterocylic, or heterocyclicalkyl; and Y is, O, S, or NH;
to yield a compound of Formula (H), or a pharmaceutically acceptable salt thereof
Another aspect of the present invention are the novel compounds of Formula (VI), and (VIII) as defined herein.

DETAILED DESCRIPTION OF THE INVENTION

The present invention relates to a novel synthesis of a group of imidazole compounds, whose general structure is shown above in Formula (I) above, and further as described in Adams et al., WO 95/02591;Adams et al., WO 96/21452, published Jul. 18, 1996;Adams et al., WO 96/21654, published Jul. 18, 1996;and Adams et al., Attorney Docket No. P50347-2, U.S. Pat. No. 5,658,903 whose disclosures are all incorporated herein by reference.

Preferred compounds of Formula (I) have the structure:

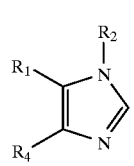
(I)

wherein
R₁ is pyrimidin-4-yl which ring is optionally substituted with one or two substituents each of which is independently selected from optionally substituted $C_{1-10}$ alkyl, optionally substituted aryl, halogen, hydroxyl, thiol, $C_{1-10}$ alkoxy, $C_{1-10}$ alkylthio, $C_{1-10}$ alkylsulfinyl, $CH_2OR_{12}$, amino, mono or di-$C_{1-10}$ alkyl substituted amino, $NHR_{21}$, $N(R_{10})C(O)R_a$ or an N-heterocyclyl ring which ring has from 5 to 7 members and optionally contains an additional heteroatom selected from oxygen, sulfur or $NR_{15}$;
R₄ is an optionally substituted phenyl, naphth-1-yl or naphth-2-yl, or heteroaryl ring;
m is 0, or the integer 1 or 2;
m' is an integer having a value of 1 or 2,
m" is 0, or an integer having a value of 1 to 5;
R₂ is -$(CR_{10}R_{20})_{n'}OR_9$, heterocyclyl, heterocyclyl$C_{1-10}$ alkyl, $C_{1-10}$alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$ alkyl, $C_{5-7}$ cycloalkenyl, $C_{5-7}$cycloalkenyl-$C_{1-10}$-alkyl, aryl, aryl$C_{1-10}$ alkyl, heteroaryl, heteroaryl-$C_{1-10}$-alkyl, $(CR_{10}R_{20})_nOR_{11}$, $(CR_{10}R_{20})_nS(O)_mR_{18}$, $(CR_{10}R_{20})_nNHS(O)_2R_{18}$, $(CR_{10}R_{20})_nNR_{13}R_{14}$, $(CR_{10}R_{20})_nNO_2$, $(CR_{10}R_{20})_nCN$, $(CR_{10}R_{20})_nSO_2R_{18}$, $(CR_{10}R_{20})_nS(O)_{m'}NR_{13}R_{14}$, $(CR_{10}R_{20})_nC(Z)R_{11}$, $(CR_{10}R_{20})_nOC(Z)R_{11}$, $(CR_{10}R_{20})_nC(Z)OR_{11}$, $(CR_{10}R_{20})_nC(Z)NR_{13}R_{14}$, $(CR_{10}R_{20})_nC(Z)NR_{11}OR_9$, $(CR_{10}R_{20})_nNR_{10}C(Z)R_{11}$, $(CR_{10}R_{20})_nNR_{10}C(Z)NR_{13}R_{14}$, $(CR_{10}R_{20})_nN(OR_6)C(Z)NR_{13}R_{14}$, $(CR_{10}R_{20})_nN(OR_6)C(Z)R_{11}$, $(CR_{10}R_{20})_nC(=NOR_6)R_{11}$, $(CR_{10}R_{20})_nNR_{10}C(=NR_{19})NR_{13}R_{14}$, $(CR_{10}R_{20})_nOC(Z)NR_{13}R_{14}$, $(CR_{10}R_{20})_nNR_{10}C(Z)NR_{13}R_{14}$, $(CR_{10}R_{20})_nNR_{10}C(Z)OR_{10}$, 5-($R_{18}$)-1,2,4-oxadizaol-3-yl or 4-($R_{12}$)-5-($R_{18}R_{19}$)-4,5-dihydro-1,2,4-oxadiazol-3-yl; wherein the aryl, arylalkyl, heteroaryl, heteroaryl alkyl, heterocyclic and heterocyclic alkyl groups may be optionally substituted;
n is an integer having a value of 1 to 10;
n' is 0, or an integer having a value of 1 to 10;
Z is oxygen or sulfur;
$R_a$ is hydrogen, $C_{1-6}$ alkyl, $C_{3-7}$ cycloalkyl, aryl, aryl$C_{1-4}$alkyl, heteroaryl, heteroaryl$C_{1-4}$alkyl, heterocyclyl, or heterocyclyl$C_{1-4}$ alkyl;

$R_3$ is heterocyclyl, heterocyclylC$_{1-10}$ alkyl or $R_8$;

$R_6$ is hydrogen, a pharmaceutically acceptable application, C$_{1-10}$ alkyl, C$_{3-7}$ cycloalkyl, aryl, arylC$_{1-4}$ alkyl, heteroaryl, heteroarylalkyl, heterocyclyl, aryl, or C$_{1-10}$ alkanoyl;

$R_8$ is C$_{1-10}$ alkyl, halo-substituted C$_{1-10}$ alkyl, C$_{2-10}$ alkenyl, C$_{2-10}$ alkynyl, C$_{3-7}$ cycloalkyl, C$_{5-7}$ cycloalkenyl, aryl, arylC$_{1-10}$ alkyl, heteroaryl, heteroarylC$_{1-10}$ alkyl, (CR$_{10}$R$_{20}$)$_n$OR$_{11}$(CR$_{10}$R$_{20}$)$_n$S(O)$_m$R$_{18}$, (CR$_{10}$R$_{20}$)$_n$NHS(O)$_2$R$_{18}$, (CR$_{10}$R$_{20}$)$_n$NR$_{13}$R$_{14}$; wherein the aryl, arylalkyl, heteroaryl, heteroaryl alkyl may be optionally substituted;

$R_9$ is hydrogen, —C(Z)R$_{11}$ or optionally substituted C$_{1-10}$ alkyl, S(0)$_2$R$_{18}$, optionally substituted aryl or optionally substituted aryl-C$_{1-4}$ alkyl;

$R_{10}$ and $R_{20}$ is each independently selected from hydrogen or C$_{1-4}$ alkyl;

$R_{11}$ is hydrogen, C$_{1-10}$ alkyl, C$_{3-7}$ cycloalkyl, heterocyclyl, heterocyclyl C$_{1-10}$ alkyl, aryl, arylthio alkyl, heteroaryl or heteroarylC$_{1-10}$ alkyl;

$R_{12}$ is hydrogen or $R_{16}$;

$R_{13}$ and $R_{14}$ is each independently selected from hydrogen or optionally substituted C$_{1-4}$ alkyl, optionally substituted aryl or optionally substituted aryl-C$_{1-4}$ alkyl, or together with the nitrogen to which they are attached form a heterocyclic ring of 5 to 7 members which ring optionally contains an additional heteroatom selected from oxygen, sulfur or NR$_9$;

$R_{15}$ is $R_{10}$ or C(Z)-C$_{1-4}$ alkyl;

$R_{16}$ is C$_{1-4}$ alkyl, halo-substituted-C$_{1-4}$ alkyl, or C$_{3-7}$ cycloalyl;

$R_{18}$ is C$_{1-10}$ alkyl, C$_{3-7}$ cycloalkyl, heterocyclyl, aryl, arylalkyl, heterocyclyl, heterocyclyl-C$_{1-10}$ alkyl, heteroaryl or heteroarylalkyl;

$R_{19}$ is hydrogen, cyano, C$_{1-4}$ alkyl, C$_{3-7}$ cycloalkyl or aryl; and $R_{21}$ is alkyl, aryl, arylC$_{1-6}$alkyl, heterocyclic, heterocyclylC$_{1-6}$ alkyl, heteroaryl, heteroarylC$_{1-6}$alkyl, wherein each of these moieties may be optionally substituted;

or a pharmaceutically acceptable salt thereof

Preferably, for compounds wherein $R_4$ is phenyl, naphth-1-yl or naphth-2-yl, or a heteroaryl, the rings are optionally substituted by one or two substituents, each of which is independently selected, and which, for a 4-phenyl, 4-naphth-1-yl, 5-naphth-2-yl or 6-naphth-2-yl substituent, is halogen, cyano, nitro, —C(Z)NR$_7$R$_{17}$, –C(Z)OR$_{16}$, —(CR$_{10}$R$_{20}$)$_v$COR$_{12}$, —SR$_5$, —SOR$_5$, —OR$_{12}$, halo-substituted-C$_{1-4}$ alkyl, C$_{1-4}$ alkyl, —ZC (Z)R$_{12}$, —NR$_{10}$C(Z)R$_{16}$, or —(CR$_{10}$R$_{20}$)$_v$NR$_{10}$R$_{20}$ and which, for other positions of substitution, is halogen, cyano, —C(Z)NR$_{13}$R$_{14}$, —C(Z) OR$_3$, —(CR$_{10}$R$_{20}$)$_{m"}$COR$_3$, —S(O)$_m$—OR$_3$, halo-substituted-C$_{1-4}$ alkyl, -C$_{1-4}$ alkyl —(CR$_{10}$R$_{20}$)$_{m"}$NR$_{10}$C(Z)R$_3$, —NR$_{10}$S(O)$_m$R$_8$, —NR$_{10}$S(O)$_{m'}$NR$_7$R$_{17}$, —ZC(Z)R$_3$ or —(CR$_{10}$R$_{20}$)$_{m"}$NR$_{13}$R$_{14}$.

Suitably, wherein $R_5$ is hydrogen, C$_{1-4}$ alkyl, C$_{2-4}$ alkenyl, C$_{2-4}$ alkynyl or NR$_7$R$_{17}$, excluding the moieties —SR$_5$ being —SR$_7$R$_{17}$ and —SOR$_5$ being —SOH.; v is 0, or an integer having a value of 1 or 2;and m" is 0, or an integer having a value of 1 to 5.

Suitably, wherein $R_7$ and $R_{17}$ are each independently selected from hydrogen or C$_{1-4}$ alkyl or $R_7$ and $R_{17}$ together with the nitrogen to which they are attached form a heterocyclic ring of 5 to 7 members which ring optionally contains an additional heteroatom selected from oxygen, sulfur or NR$_{15}$.

Suitably, $R_{15}$ is $R_{10}$ or C(Z)-C$_{1-4}$ alkyl, and $R_{10}$ and Z are as defined for Formula (I).

The compounds of Formula (I) may be used in association with the treatment of cytokine mediated diseases in a mammal, or for the veterinary treatment of mammals who are in need of inhibition of cytokine production.

Another embodiment of the present invention are the novel compounds of the Formula (VI) having the structure:

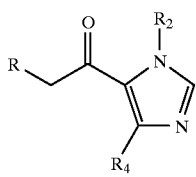

(VI)

wherein

R is optionally substituted C$_{1-10}$ alkyl, optionally substituted aryl, halogen, hydroxyl, thiol, C$_{1-10}$ (alkoxy, C$_{1-10}$ alkylthio, C$_{1-10}$ alkylsulfinyl, CH$_2$OR$_{12}$amino, mono or di-C$_{1-6}$ alkyl substituted amino, NHR$_{21}$, N(R$_{10}$)C(O)R$_a$ or an N-heterocyclyl ring which ring has from 5 to 7 members and optionally contains an additional heteroatom selected from oxygen, sulfur or NR$_{15}$;

$R_a$ is hydrogen, C$_{1-6}$ alkyl, C$_{3-7}$ cycloalkyl, aryl, arylC$_{1-4}$ alkyl, heteroaryl, heteroarylC$_{1-4}$alkyl, heterocyclyl, or heterocyclylC$_{1-4}$ alkyl;

$R_4$ is an optionally substituted phenyl, naphth-1-yl or naphth-2-yl, or heteroaryl ring;

$R_2$ is -(CR$_{10}$R$_{20}$)n'OR$_9$, heterocyclyl, heterocyclylC$_{1-10}$alkyl, C$_{1-10}$alkyl, halo-substituted C$_{1-10}$ alkyl, C$_{2-10}$ alkenyl, C$_{2-10}$ alkynyl, C$_{3-7}$ cycloalkyl, C$_{3-7}$cycloalkylC$_{1-10}$ alkyl, C$_{5-7}$ cycloalkenyl, C$_{5-7}$cycloalkenyl-C$_{1-10}$ alkyl, aryl, arylC$_{1-10}$ alkyl, heteroaryl, heteroaryl-C$_{1-10}$ alkyl, (CR$_{10}$R$_{20}$)$_n$OR$_{11}$, (CR$_{10}$R$_{20}$)$_n$S(O)$_m$R$_{18}$, (CR$_{10}$R$_{20}$)$_n$NHS(O)$_2$R$_{18}$, (CR$_{10}$R$_{20}$)$_n$NR$_{13}$R$_{14}$, (CR$_{10}$R$_{20}$)$_n$NO$_2$, (CR$_{10}$R$_{20}$)$_n$CN, (CR$_{10}$R$_{20}$)$_{n"}$SO$_2$R$_{18}$, (CR$_{10}$R$_{20}$)$_n$S(O)$_{m"}$NR$_{13}$R$_{14}$, (CR$_{10}$R$_{20}$)$_n$C(Z)R$_{11}$, (CR$_{10}$R$_{20}$)$_n$OC(Z)R$_{11}$, (CR$_{10}$R$_{20}$)$_n$C(Z)OR$_{11}$, (CR$_{10}$R$_{20}$)$_n$C(Z)NR$_{13}$R$_{14}$, (CR$_{10}$R$_{20}$)$_n$C(Z)NR$_{11}$ OR$_9$, (CR$_{10}$R$_{20}$)$_n$NR$_{10}$C(Z)R$_{11}$, (CR$_{10}$R$_{20}$)$_n$NR$_{10}$C(Z)NR$_{13}$R$_{14}$, (CR$_{10}$R$_{20}$)$_n$N(OR$_6$)C(Z)NR$_{13}$R$_{14}$, (CR$_{10}$R$_{20}$)$_n$N(OR$_6$)C(Z)R$_{11}$, (CR$_{10}$R$_{20}$)$_n$C(=NOR$_6$)R$_{11}$(CR$_{10}$R$_{20}$)$_n$NR$_{10}$C(=NR$_{19}$)NR$_{13}$R$_{14}$, (CR$_{10}$R$_{20}$)$_n$OC(Z)NR$_{13}$R$_{14}$, (CR$_{10}$R$_{20}$)$_n$NR$_{10}$C(Z) NR$_{13}$R$_{14}$, (CR$_{10}$R$_{20}$)$_n$NR$_{10}$C(Z)OR$_{10}$, 5-(R$_{18}$)-1,2,4-oxadizaol-3-yl or 4-(R$_{12}$)-5-(R$_{18}$R$_{19}$)4,5-dihydro-1,2,4-oxadiazol-3-yl; wherein the aryl, arylalkyl, heteroaryl, heteroaryl alkyl, heterocyclic and heterocyclic alkyl groups may be optionally substituted;

n is an integer having a value of 1 to 10 n' is 0, or an integer having a value of 1 to 10;

m' is an integer having a value of 1 or 2,

Z is oxygen or sulfur;

$R_9$ is hydrogen, —C(Z)R$_{11}$ or optionally substituted C$_{1-10}$ alkyl, S(O)$_2$R$_{18}$, optionally substituted aryl or optionally substituted aryl-C$_{1-4}$ alkyl;

$R_{10}$ and $R_{20}$ is each independently selected from hydrogen or C$_{1-4}$ alkyl;

$R_{11}$ is hydrogen, C$_{1-10}$ alkyl, C$_{3-7}$ cycloalkyl, heterocyclyl, heterocyclyl C$_{1-10}$ alkyl, aryl, arylC$_{1-10}$ alkyl, heteroaryl or heteroarylC$_{1-10}$ alkyl;

$R_{12}$ is hydrogen or $R_{16}$;

$R_{13}$ and $R_{14}$ is each independently selected from hydrogen or optionally substituted $C_{1-4}$ alkyl, optionally substituted aryl or optionally substituted aryl-$C_{1-4}$ alkyl, or together with the nitrogen to which they are attached form a heterocyclic ring of 5 to 7 members which ring optionally contains an additional heteroatom selected from oxygen, sulfur or $NR_9$;

$R_{15}$ is $R_{10}$ or $C(Z)$-$C_{1-4}$ alkyl;

$R_{16}$ is $C_{1-4}$ alkyl, halo-substituted-$C_{1-4}$ alkyl, or $C_{3-7}$ cycloalkyl;

$R_{18}$ is $C_{1-10}$ alkyl, $C_{3-7}$ cycloalkyl, heterocyclyl, aryl, arylalkyl, heterocyclyl, heterocyclyl-$C_{1-10}$ alkyl, heteroaryl or heteroarylalkyl;

$R_{19}$ is hydrogen, cyano, $C_{1-4}$ alkyl, $C_{3-7}$ cycloalkyl or aryl; and $R_{21}$ is alkyl, aryl, aryl$C_{1-6}$alkyl, heterocyclic, heterocyclyl¢$C_{1-6}$ alkyl, heteroaryl, heteroaryl$C_{1-6}$alkyl, wherein each of these moieties may be optionally substituted.

Yet another embodiment of the present invention are the novel compounds of Formula (VIII) having the structure:

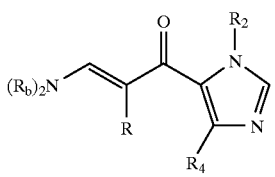

(VIII)

wherein $R_b$ is alkyl, aryl, heteroaryl, cycloalkyl, cycloalkenyl, arylalkyl, heteroarylalkyl, heterocylic, or heterocyclicalkyl, all of which may be optionally substituted;

R is optionally substituted alkyl, optionally substituted aryl, $_{1-4}$ alkyl, halogen, hydroxyl, thiol, $C_{1-4}$ alkoxy, $C_{1-4}$ alkylthio, $C_{1-4}$ alkylsufinyl, $CH_2OR_{12}$, amino, mono or di-$C_{1-6}$ alkyl substituted amino, $NHR_{21}$, $N(R_{10})C(O)R_a$ or an N-heterocyclyl ring which ring has from 5 to 7 members and optionally contains an additional heteroatom selected from oxygen, sulfur or $NR_{15}$;

$R_a$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl;

$R_4$ is an optionally substituted phenyl, naphth-1-yl or naphth-2-yl, or heteroaryl ring;

$R_2$ is -$(CR_{10}R_{20})_{n'}OR_9$, heterocyclyl, heterocyclyl$C_{1-10}$ alkyl, $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$ alkyl, $C_{5-7}$ cycloalkenyl, $C_{5-7}$cycloalkenyl$_{1-10}$-alkyl, aryl, aryl$C_{1-10}$ alkyl, heteroaryl, heteroaryl-$C_{1-10}$ -alkyl, $(CR_{10}R_{20})_nOR_{11}$, $(CR_{10}R_{20})_nS(O)_mR_{18}$, $(CR_{10}R_{20})_nNHS(O)_2R_{18}$, $(CR_{18}R_{20})_nNR_{13}R_{14}$, $(CR_{10}R_{20})_nNO_2$, $(CR_{10}R_{20})_nCN$, $(CR_{10}R_{20})_{n'}SO_2R_{18}$, $(CR_{10}R_{20})_nS(O)_{m'}NR_{13}R_{14}$, $(CR_{10}R_{20})_nC(Z)R_{11}$, $(CR_{10}R_{20})_nOC(Z)R_{11}$, $(CR_{10}R_{20})_nC(Z)OR_{11}$, $(CR_{10}R_{20})_nC(Z)NR_{13}R_{14}$, $(CR_{10}R_{20})_nC(Z)NR_{11}OR_9$, $(CR_{10}R_{20})_nNR_{10}C(Z)R_{11}$, $(CR_{10}R_{20})_nNR_{10}C(Z)NR_{13}R_{14}$, $(CR_{10}R_{20})_nN(OR_6)C(Z)NR_{,13}R_{14}$, $(CR_{10}R_{20})_nN(OR_6)C(Z)R_{11}$, $(CR_{10}R_{20})_nC(=NOR_6)R_{11}$, $(CR_{10}R_{20})_nNR_{10}C(=NR_{19})NR_{13}R_{14}$, $(CR_{10}R_{20})_nOC(Z)NR_{13}R_{14}$, $(CR_{10}R_{20})_nNR_{10}C(Z)NR_{13}R_{14}$, $(CR_{10}R_{20})_nNR_{10}C(Z)OR_{10}$, 5-$(R_{18})$-1,2,4-oxadizaol-3-yl or 4-$(R_{12})$-5-$(R_{18}R_{19})$-4,5-dihydro- 1,2, 4oxadiazol-3-yl; wherein the aryl, arylalkyl, heteroaryl, heteroaryl alkyl, heterocyclic and heterocyclic alkyl groups may be optionally substituted;

n is an integer having a value of 1 to 10 n' is 0, or an integer having a value of 1 to 10;

m' is an integer having a value of 1 or 2,

Z is oxygen or sulfur;

$R_9$ is hydrogen, —$C(Z)R_{11}$ or optionally substituted $C_{1-10}$ alkyl, $S(O)_2R_{18}$, optionally substituted aryl or optionally substituted aryl-$C_{1-4}$ alkyl;

$R_{10}$ and $R_{20}$ is each independently selected from hydrogen or $C_{1-4}$ alkl;

$R_{11}$ is hydrogen, $C_{1-10}$ alkyl, $C_{3-7}$ cycloalkyl, heterocyclyl, heterocyclyl $C_{1-10}$ alkyl, aryl, aryl$C_{1-10}$alkyl, heteroaryl or heteroaryl$C_{1-10}$ alkyl;

$R_{12}$ is hydrogen or $R_{16}$;

$R_{13}$ and $R_{14}$ is each independently selected from hydrogen or optionally substituted $C_{1-4}$ alkyl, optionally substituted aryl or optionally substituted aryl-$C_{1-4}$ alkyl, or together with the nitrogen to which they are attached form a heterocyclic ring of 5 to 7 members which ring optionally contains an additional heteroatom selected from oxygen, sulfur or $NR_9$;

$R_{15}$ is $R_{10}$ or $C(Z)$-$C_{1-4}$ alkyl;

$R_{16}$ is $C_{1-4}$ alkyl, halo-substituted-$C_{1-4}$ alkyl, or $C_{3-7}$ cycloalkyl;

$R_{18}$ is $C_{1-10}$ alkyl, $C_{3-7}$ cycloalkyl, heterocyclyl, aryl, arylalkyl, heterocyclyl, heterocyclyl-$C_{1-10}$alkyl, heteroaryl or heteroarylalkyl;

$R_{19}$ is hydrogen, cyano, $C_{1-4}$ alkl, $C_{3-7}$ cycloalkyl or aryl;

$R_{21}$ is $C_{1-6}$ alkyl, aryl, aryl$C_{1-6}$alkyl, heterocyclic, heterocyclyl$C_{1-6}$ alkyl, heteroaryl, heteroaryl$C_{1-6}$alkyl, wherein each of these moieties may be optionally.

Unless otherwise defined in any of the references incorporated herein, the term "optionally substituted" as used herein shall mean such groups as halogen, such as fluorine, chlorine, bromine or iodine; hydroxy; hydroxy substituted $C_{1-10}$alkyl;$C_{1-10}$ alkoxy, such as methoxy or ethoxy; $S(O)m$ alkyl, wherein m is 0, 1 or 2, such as methyl thio, methylsulfinyl or methyl sulfonyl; amino, mono & di-substituted amino, such as in the $NR_7R_{17}$ group; or where the $R_7R_{17}$ may together with the nitrogen to which they are attached cyclized to form a 5 to 7 membered ring which optionally includes an additional heteroatom selected from O/N/S; $C_{1-10}$ alkyl, cycloalkyl, or cycloalkyl alkyl group, such as methyl, ethyl, propyl, isopropyl, t-butyl, etc. or cyclopropyl methyl; halosubstituted $C_{1-10}$ alkyl, such $CF_2CF_2H$, or $CF_3$;an optionally substituted aryl, such as phenyl, or an optionally substituted arylalkyl, such as benzyl or phenylethyl, wherein these aryl moieties may also be substituted one to two times by halogen; hydroxy; hydroxy substituted alkyl; $C_{1-10}$ alkoxy; $S(O)_m$ alkyl; amino, mono & di-substituted amino, such as in the $NR_7R_{17}$ group; alkyl, or $CF_3$.

A general method of synthesis for compounds of Formula (I) is shown below Scheme 1.

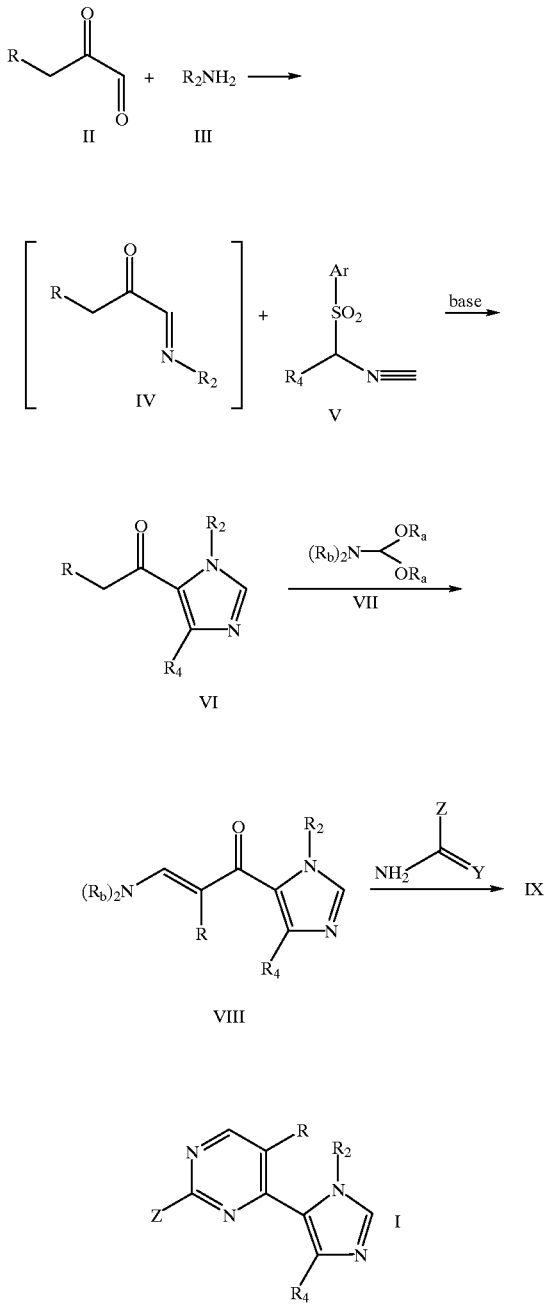

Scheme 1

The synthesis provided for in these Schemes is applicable for the producing compounds of Formula (I) having a variety of different $R_1$, $R_2$, and $R_4$ groups which are reacted, employing optional substituents which are suitably protected, to achieve compatibility with the reactions outlined herein. Subsequent deprotection, in those cases, then affords compounds of the nature generally disclosed. Once the imidazole nucleus has been established, further compounds of Formula (I) may be prepared by applying standard techniques for functional group interconversion, well known in the art. For instance, on the pyrimidine ring, halogen from OH, by reacting with $POX_3$ or $PX_3$, wherein X is halogen; $C_{1-4}$ alkylsulfinyl from $C_{1-4}$ alkylthio by oxidation of the sulfur with an appropriate oxidant; $N(R_{10})C(O)R_a$ from $NH(R_{10})$ by acylation on nitrogen with an appropriate acylating agent; $YC(O)R_a$ where Y is any leaving group. For other alternative groups on the $R_2$ or $R_4$ moiety, such as —$C(O)NR_{13}R_{14}$ from -$CO_2CH_3$ by heating with or without catalytic metal cyanide, e.g. NaCN, and $HNR_{13}R_{14}$ in $CH_3OH$; —$OC(O)R_3$ from —OH with e.g., $ClC(O)R_3$ in pyridine; —$NR_{10}$-$C(S)NR_{13}R_{14}$ from —$NHR_{10}$ with an alkylisothiocyante or thiocyanic acid; $NR_6C(O)OR_6$ from —$NHR_6$ with the alkyl chloroformate; —$NR_{10}C(O)NR_{13}R_{14}$ from —$NHR_{10}$ by treatment with an isocyanate, e.g. HN=C=O or $R_{10}$ N=C=O; —$NR_{10}$—$C(O)R_8$ from —$NHR_{10}$ by treatment with Cl—$C(O)R_3$ in pyridine; —$C(=NR_{10})NR_{13}R_{14}$ from —$C(NR_{13}R_{14})SR_3$ with $H_3NR_3{}^+OAc^-$ by heating in alcohol; —$C(NR_{13}R_1)SRE3$ from —$C(S)NR_{13}R_{14}$ with $R_6$-I in an inert solvent, e.g. acetone; —$C(S)NR_{13}R_{14}$ (where $R_{13}$ or $R_{14}$ is not hydrogen) from —$C(S)NH_2$ with $HNR_{13}R_{14}$—$C(=NCN)$—$NR_{13}R_{14}$ from —$C(=NR_{13}R_{14})$ —$SR_3$ with $NH_2CN$ by heating in anhydrous alcohol, alternatively from —$C(=NH)$—$NR_{13}R_{14}$ by treatment with BrCN and NaOEt in EtOH; —$NR_{10}$—$C(=NCN)SR_8$ from —$NHR_{10}$ by treatment with $(R_8S)_2C=NCN$; —$NR_{10}SO_2R_3$ from —$NHR_{10}$ by treatment with $ClSO_2R_3$ by heating in pyridine; —$NR_{10}C(S)R_3$ from —$NR_{10}C(O)R_8$ by treatment with Lawesson's reagent [2,4-bis(4-methoxyphenyl)-1,3,2,4-dithiadiphosphetane-2,4-disulfide]; —$NR_{10}SO_2CF_3$ from —$NHR_6$ with triflic anhydride and base wherein $R_3$, $R_6$, $R_{10}$, $R_{13}$ and $R_{14}$ are as defined in Formula (I) herein.

Precursors of the groups $R_1$, $R_2$ and $R_4$ can be other $R_1$, $R_2$ and $R_4$ groups which can be interconverted by applying standard techniques for functional group interconversion. For example a compound of the formula (I) wherein $R_2$ is halo-substituted $C_{1-10}$ alkyl can be converted to the corresponding $C_{1-10}$ alkyl$_3$ derivative by reacting with a suitable azide salt, and thereafter if desired can be reduced to the corresponding $C_{1-10}$alkyl $NH_2$ compound, which in turn can be reacted with $R_{18}S(O)_2X$ wherein X is halo (e.g., chloro) to yield the corresponding $C_{1-10}$alkylNHS(O)$_2R_{18}$ compound.

Alternatively a compound of the formula (I) wherein $R_2$ is halo-substituted $C_{1-10}$-alkyl can be reacted with an amine $R_{13}R_{14}NH$ to yield the corresponding $C_{1-10}$—alkyl$NR_{13}R_{14}$ compound, or can be reacted with an alkali metal salt of $R_{18}SH$ to yield the corresponding $C_{1-10}$alkyl$SR_{18}$ compound.

In Scheme I the compounds of Formula (I) are suitably prepared by reacting a compound of the Formula (II) with a compound of the Formula (III) wherein R is any suitable group, such as H, alkyl, substituted alkyl, aryl, aryl alkyl, heterocyclic, heterocylic alkyl, heteroaryl, heteroarylalkyl, cycloalkyl, or amino, and $R_2$ is as defined herein, for Formula (I), or is a precursor of the group $R_2$, and thereafter if necessary converting a precursor of $R_2$ to the desired $R_2$ group. Suitable precursor groups of $R_2$ include various well known protecting groups, particularly when $R_2$ is a nitrogen containing heterocyclic ring, such as piperidine. Suitable protecting groups are described in many references, for instance, Protecting Groups in Organic Synthesis, Greene T W, Wiley-Interscience, New York, 1981. When $R_2$ is an optionally substituted cycloakyl, such as a 4-hydroxy-cyclohexyl, the precursor cyclohexanone could be used, and then reduced to the alcohol.

The compounds of Formula (IV) which are formed are either isolated, or more suitably reacted in situ with compounds of the Formula (V) and a suitable base, where Ar is an optionally substituted phenyl group and $R_4$ is defined herein, for compounds of Formula (I), to produce compounds of the Formula (VI). Heating compounds of the Formula (VI) with an enaminating reagent such as a compound of Formula (VII), or derivatives thereof, such as reagents of similar structure and reactivity to DMFDMA which include tris(dimethylamino)methane or tert-butoxybis(dimethylamino)-methane, or any other reactive species known to behave as enaminating agents; which produces compounds of the Formula (VI), which can be isolated, or more preferably reacted in situ with reagents of Formula (IX), where Y and Z are defined for Formula (IX) above to produce the compounds of Formula (I).

An alternative to using reagents of Formula (VII) to produce an enamine of Formula (VIII) is to react compounds of Formula (VI) with formylating agents, such as formate esters, or formamides, to produce 1,3-dicarbonyl compounds which, when in their tautomeric form, are similar to compounds of the Formula (VIII), where $(R_b)_2N=OR$, wherein R is alkyl, alkyl, aryl, heteroaryl, cycloalkyl, cycloalkenyl, arylalkyl, heteroarylalkyl, heterocylic, heterocyclicalkyl, or silyl. Compounds of the Formula (VIII), where $(R_b)_2N=OR$ can be reacted directly with reagents of the Formula (IX) to produce compounds of the Formula (I).

The process is exemplified, in Scheme I, by reaction of pyruvaldehyde (Formula II, R=H), which is typically obtained as an aqueous solution, with a primary amine (Formula III) in a solvent to produce imines of the Formula (IV), employing a modification of the method of van Koten (see van der Poel and van Koten, *Synth. Commun.* 1978, 8, 305 whose disclosure is incorporated by reference herein in its entirety). Suitable solvents for this process include, but are not limited to, ethereal solvents, such as tetrahydrofuran (THF), t-butyl methyl ether TBME), diethyl ether, acetonitrile (MeCN), ethyl acetate (EtOAc), N,N,-dimethylformamide (DMF), and dimethylsulfoxide (DMSO). The reaction requires times of ~1 min to about 24 h, with the preferred times being from about 10–20 min. The reaction is suitably conducted at temperatures ranging from about 0° C. to room temperature, or may be performed at elevated temperatures, of at least 100° C., if so desired.

Imines of Formula (IV) can be dissolved in a solvent and reacted with compounds of Formula (V), with or without added base, to produce compounds of Formula (VI). A suitable base for this reaction is potassium carbonate, or those noted below and suitable solvents include DMF and DMSO as noted below. The reaction can be conducted at 0° C., room temperature or as high as about 65° C.

A further embodiment of the present invention involves the preparation of the imines of the Formula (IV) in situ, followed by reaction with isonitriles of the Formula (V) to produce imidazoles of the Formula (VI). In this process, aldehydes of Formula (II) are combined with primary amines of Formula (III) in a suitable solvent, and after the prescribed amount of time the imine formation is considered complete and isonitriles of the Formula (V) and a suitable base are added. Suitable solvents include, but are not limited to, acetonitrile, THF, MeCN, toluene, EtOAc, DMF, and DMSO and mixtures thereof. The imine formation requires times of ~5 min to about 6 hours, with the preferred times being about 10–20 min and can be conducted at temperatures ranging from about 0° C. to 60° C. After addition of the isonitrile, the reaction typically requires an additional 2 to 24 hours at temperatures of 0° C. to 65° C. to go to completion. The reaction proceeds without bases or in the presence of suitable bases, including but not limited to including inorganic and organic amine bases, such as potassium carbonate, sodium carbonate, $K_3PO_4$, $K_2HPO_4$, $Na_2HPO_4$, including inorganic and organic amine bases, such as secondary amines, e.g. morpholine, pyrrolidine, piperidine, and tertiary amines, such as DBU or DBM, as well as tetraethyl guanidine.

Imidazoles of the Formula (VI) can be converted to compounds of the Formula (VIII) by the action of agents of the Formula (VII), or agents of similar structure and reactivity. The process involves heating compounds of Formula (VI) with N,N-dimethylformamide dimethyl acetal (DMFDMA) with no solvent, or a suitable solvent, at temperatures higher than about 70° C. Suitable solvents include, but are not limited to toluene, ethanol, 1-propanol, 2-propanol, DMF, and DMSO. Reagents of similar structure and reactivity to DMFDMA include tris(dimethylamino) methane or tert-butoxybis(dimethylamino)methane, or other reactive species know to behave as enaminating agents. With some of the more reactive enaminating reagents, the temperature for this process can be lower than the 70° C. mentioned above.

Compounds of the Formula (VIII) can be isolated, or prepared in situ, and reacted further as shown in Scheme 1. In either case, the reaction involves reacting compounds of Formula (VIII) with compounds of Formula (IX) in a suitable solvent, and a suitable base, if necessary. Suitable solvents include, but are not limited to, alcohols, such as methanol, ethanol, 1-propanol and 2-propanol, toluene, alone or in combination with an alcohol, DMF, DMSO, or combinations of the above. Reagents of the Formula (IX), when Y is NH, are typically obtained as an acid salt, and as such, require the action of a base to react with compounds of the Formula (VIII). When Y is O or S, the reaction may require either acid or base catalysis. Suitable bases include, but are not limited to, NaOMe, NaOEt, potassium carbonate, and KOH. Temperatures of about 25 to about 110° C. have been found to be useful for this conversion, with temperatures>65° C. being preferred.

A further embodiment of the present invention involves the preparation of imidazoles of the Formula (I) as shown in Scheme 1 in a single pot. The reaction conditions mentioned above are generally suitable for conducting the synthesis in one pot, with one modification. The conversion of compounds of the Formula (VI) to compounds of the Formula (VIII) requires anhydrous conditions. Water is introduced into the reaction when using pyruvaldehyde (II, R=H) as it is sold as a solution in water, which must be removed before proceeding. Following complete conversion of (IV) and (V) to form (VI), suitable methods of dehydration include, but are not limited to the following: using excess DMFDMA (~10 equivalents) to both react with water and then with ketones (VI); azeotropically removing water with cosolvents such as toluene, or alcohols; adding other drying agents such as MgSO4;or triethyl orthoformate.

SYNTHETIC EXAMPLES

The invention will now be described by reference to the following examples which are merely illustrative and are not to be construed as a limitation of the scope of the present invention. All temperatures are given in degrees centigrade, all solvents are highest available purity and all reactions run under anhydrous conditions in an argon atmosphere unless otherwise indicated.

In the Examples, all temperatures are in degrees Centigrade (° C.). Mass spectra were performed upon a VG Zab mass spectrometer using fast atom bombardment, unless otherwise indicated. $^1$H-NMR (hereinafter "NMR") spectra were recorded at 300 MHz using a Bruker AM 300 spectrometer. Multiplicities indicated are: s=singlet, d=doublet, t=triplet, q=quartet, m=multiplet and br indicates a broad signal. Sat. indicates a saturated solution, eq indicates the proportion of a molar equivalent of reagent relative to the principal reactant. Flash chromatography is generally run over Merck Silica gel 60 (230–400 mesh).

EXAMPLE 1

Ethyl 4-(2-oxopropylidene)amino-1-piperidinecarboxylate

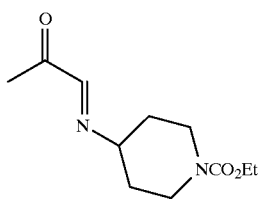

To a solution of pyruvaldehyde (40% w/w solution in water, 2.67 mL, 3.15 g, 17.5 mol) in 50 ml of Et$_2$O at room temperature was added dropwise ethyl 4-aminopiperidecarboxylate (3.0 mL, 3.01 g, 17.5 mmol). After 20 min, the solution was diluted with 50 mL of Et$_2$O and washed with 3×30 mL of water. The solution was concentrated in vacuo to yield 2.3 g (58%) of the imine product which was used as such in the subsequent step: $^1$H NMR (CDCl$_3$) δ7.58 (1H, s), 4.07 (2H, q, J=7.1 Hz)), 4.04 (2H, m), 3.39 (1H, m), 3.02 (2H, m), 2.31 (3H, s), 1.65 (4H, m), 1.19 (3H, t, J=7.1 Hz).

Example (Ia): Alternative conditions utilized in above noted synthesis include MeCN as solvent and mixing the reagents at 0° C.

EXAMPLE 2

1-(1-Ethoxycarbonyl-4-piperidinyl)-4-(4-fluorophenyl)-5-acetylimidazole:

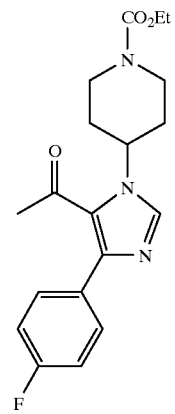

To a solution of the imine described in Example 1 above (1.12 g, 4.95 mmol) in 9 mL of DMF at room temperature was added α-(p-toluenesulfonyl)-4 -fluorobenzylisonitile (1.30 g, 4.50 mmol) and K$_2$CO$_3$ (0.68 g, 4.95 mmol). After 22 h, the solution was diluted with 75 mL of EtOAc and washed with 2×60 mL of 3N HCl. The aqueous layers were combined and basified with excess solid K$_2$CO$_3$ until the bubbling ceased. The aqueous layer was transferred to a separatory funnel and extracted 2×75 mL of EtOAc. The combined organics were washed with 3×50 mL of water and concentrated in vacuo. The residue was recrystallized from CHCl$_3$/Hexane to yield the imidazole product (1.05 g, 65%) which was used in subsequent steps: mp=118-19 ° C.; IR (KBr) 1691, 1681, 1640 cm$^{-1}$,$^1$H NMR (CDCl$_3$) δ7.74 (1H,s), 7.44 (2H, m), 7.14 (2H, t, J=8.6 Hz), 5.00 (1H, tt, J=3.7, 12.1Hz), 4.35 (2H, m), 4.17 (2H, q, J=7.1 Hz), 2.93 (2H, m), 2.18 (2H, br d, J=12.9 Hz), 2.12 (3H, s), 1.80 (2H, dq, J=4.2, 12.4 Hz), 1.28 (3H, t, J=7.1 Hz); $^{13}$C NMR (CDCL$_3$) d 191.00, 164.74, 161.45, 155.31, 149.77, 137.39, 131.46, 131.35, 126.99, 115.63, 115.34, 61.59, 54.85, 43.29, 33.40, 30.45, 14.63; $^{13}$C NMR (CDCl$_3$) δ191.00, 164.75, 161.45, 155.31, 149.77, 137.39, 131.46, 131.35, 126.99, 115.63, 115.35, 61.59, 54.85, 43.29, 33.40,30.45, 14.63; Anal. Calcd for C$_{19}$H$_{22}$N$_3$O$_3$F: C, 63.5; H; 6.2; N, 11.7. Found C, 63.1; H, 63.1; H, 6.1; N, 11.5.

In an alternative procedure to that listed above, the title compound was prepared in the following manner: To a solution of pyruvaldehyde (40% w/w solution in water, 3.97 mL, 4.68 g, 25.94 mmol) in 34 mL of DMSO at room temperature was added dropwise ethyl 4-ano-piperidinecarboxylate (4.45 mL, 4.47 g, 25.94 mmol). After 10 min α-(p-toluenesulfonyl)-4-fluoro-benzylisonitrile (5.0 g, 17.3 mmol) and K$_2$CO$_3$ (2.39 g, 17.3 mmol) were added. After 15 h, the solution was diluted with 100 mL of EtOAc and washed with 2×10 mL of 3N HCl. The aqueous layers were combined and basified with excess solid K$_2$CO$_3$ until the bubbling ceased. The aqueous layer was transferred to a separatory funnel and extracted 2×150 mL of EtOAc. The combined organics were washed with 3×75 ml of water and concentrated in vacuo to yield the imidazole product (4.65 g, 75%) which was used as is in subsequent steps.

Alternative conditions for this synthesis include the Examples shown below:

| Solvent | Base/eq | Temp for imine formation | Temp for cycloaddition | Imine formation time |
|---|---|---|---|---|
| DMF | $K_2CO_3$/1.2 | room temp. | room temp. | 15 min |
| DMF | $K_2CO_3$/1.1 | room temp. | room temp. | 15 min |
| DMF | $K_2CO_3$/1.2 | room temp. | room temp. | 20 min |
| DMF | $K_2CO_3$/1.2 | room temp. | room temp. | 17 min. |
| DMF | $K_2CO_3$/1.2 | room temp. | room temp. | 80 min |
| DMF | $K_2CO_3$/1.2 | room temp. | room temp. | 75 min |
| DMF | $K_2CO_3$/1.2 | room temp. | room temp. | 6 h |
| DMF | $K_2CO_3$/1.2 | room temp. | room temp. | 2 h |
| DMF | $K_2CO_3$/1.1 | room temp. | room temp. | 85 min |
| DMF | $K_2CO_3$/1.2 | room temp. | room temp. | 12 min |
| DMF | $K_2CO_3$/1.2 | 45° C. | 45° C. | 12 min |
| DMF | $K_2CO_3$/1.2 | 60° C. | 60° C. | 14 min |
| DMF/$MgSO_4$ | $K_2CO_3$/1.2 | room temp. | room temp. | 12 min |
| DMF | $K_2CO_3$/1.2 | room temp. to 40° C., distill | room temp. | 12 min |
| DMF | $K_2CO_3$/1.1 | 40° C. | 40° C. | 10 min. |
| DMF | $K_2CO_3$/1.25 | 0° C. | room temp. | 4 h |
| DMF | $K_2CO_3$/1.2 | 0° C. | 0° C. | 2.33 h |
| DMF | $NaHCO_3$/1.3 | room temp. | room temp. | 75 min. |
| MeCN | $K_2CO_3$/1.25 | room temp. | room temp. | 25 min. |
| MeCN | $K_2CO_3$/1.2 | room temp. | room temp. | 5 min. |
| MeCN | $K_2CO_3$/1.2 | room temp. | room temp. | 10 min. |
| MeCN | $K_2CO_3$/1.25 | 0° C. | room temp. | 15 min. |
| MeCN | $K_2CO_3$/1.2 | 0° C. | 0° C. | 145 min. |
| DMSO | $K_2CO_3$/1.25 | room temp. | room temp. | 15 min. |
| THF | morpholine/3 | room temp. | room temp. | 1 h |
| THF | $K_2CO_3$/1.2 | 0° C. | 0° C. | 145 min. |
| Toluene | $K_2CO_3$/1.25 | room temp. | room temp. | 15 min. |
| EtOAc | $K_2CO_3$/1.0 | room temp. | room temp. | 11 min. |

EXAMPLE 3

1-(1-Ethoxycarbonyl-4-piperidinyl)-4-(4-fluorophenyl)-5-(3-N,N-dimethylano-trans-1-propenone) imidazole

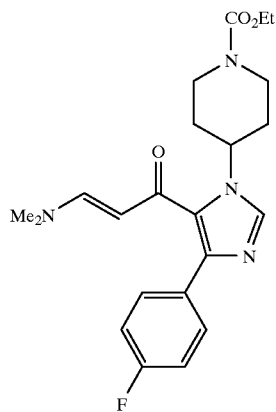

The ketoimidazole prepared in Example 2 above (0.4 g, 1.11 mmol) was dissolved in 4 mL of DMSO and N,N-dimethylformamide dimethyl acetal (0.18 mL, 0.16 g, 1.33 mmol) and was heated at 90° C. for 5.5 h. The solution was cooled to room temperature and the solvents were removed under vacuum by Kugel-Rohr distillation. The residue was purified by preparative TLC using hexanes/ethyl acetate (1:1) and eluting twice to give 0.3 g (65%) of the title compound as a brown solid: $^1$H NMR ($CDCl_3$) δ7.65 (1H, s), 7.55 (2H, m), 7.48 (1H, m), 7.02 (2H, t, J=8.7 Hz), 5.02 (1H, d, J=12.6 Hz), 4.91 (1H, m), 4.30 (2H, m), 4.13 (2H, q, J=7.1 Hz), 2.99 (3H, br s), 2.89 (2H, m), 2.51 (3H, br s), 2.18 (2H, d, J=12.1 Hz), 1.78 (2H, dq, J=4.3, 12.3 Hz), 1.26 (3H, t, J=7.1 Hz).

EXAMPLE 4

1-(1-Ethoxycarbonyl-4-piperidinyl)4-(4-fluorophenyl)-5-{2-(methylamino)-4-pyrimidinyl}imidazole:

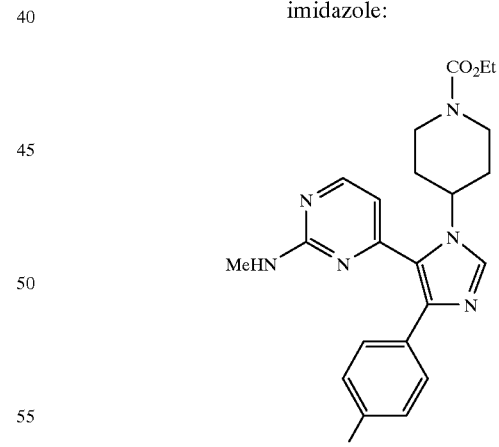

To a solution of the ketoimidazole prepared in Example 2 above (2.1 g, 5.85 mmol) in 10.5 mL of 1-propanol was added N,N-dimethylformamide dimethyl acetal (1.32 mL, 1.18 g, 9.94 mmol) and the solution was heated at 100° C. for 6 h. At this time, TLC indicated no starting material and N-methylguanidine•HCl (0.96 g, 8.77 mmol) and NaOEt (21% w/w solution, 3.50 mL, 3.05 g, 9.35 mmol) were added. After 18 hours, the solution was cooled to room temperature, diluted with 40 mL of water, 50 mL of 3N HCl and 50 mL of EtOAC. The layers were separated and the organic layer wash washed again with 20 mL of 3N HCl. The combined aqueous layers were basified with solid $K_2CO_3$ until bubbling ceased. The aqueous layer was extracted with EtOAc (2×50 mL). The combined organics were washed with 3×100 mL of water, concentrated and the residue was recrystallized from EtOAc to give 1.24 g (50%) of the title compound: mp=205–206° C.; IR (KBr) 3242, 3110, 1695, 1588, 1568, 1532, 1507 cm$^{-1}$; $^1$H NMR (CDCl$_3$) δ8.15 (1H, d, J=5.0 Hz), 7.71 (1H, s), 7.44 (2H, m), 6.97 (2H, t, J=8.7 Hz), 6.40 (1H, d, J=5.0 Hz), 5.18 (1H, m), 4.83 (1H, m), 4.34 (2H, m), 4.15 (2H, q, J=7.1 Hz), 3.02 (3H, d, J=5.0 Hz), 2.81 (2H, m), 2.19 (2H, m), 1.87 (2H, dq, J=4.4, 12.5 Hz), 1.27 (3H, t, J=7.1 Hz); $^{13}$C NMR (CDCl$_3$) δ164.00, 163.03, 160.73, 158.51, 158.32, 155.31, 141.96, 135.57, 130.52, 130.07, 129.97, 125.01, 115.39, 115.11, 111.73, 61.61, 53.80, 43.42, 33.43, 28.43, 14.63; Anal. Cald for $C_{22}H_{25}N_6O_2F$; C, 62.2; H, 5.9; N, 19.8; Found C, 61.9, H, 6.0; N, 19.4.

Examples 4 (a) and (b) include the alternative conditions

| Solvent | DMFDMA temp | Base | Pyrimidine temp. |
|---------|-------------|------|------------------|
| EtOH    | 85° C.      | NaOMe | 85 ° C.         |
| DMF     | 100° C.     | NaOMe | 65 ° C.         |

EXAMPLE 5

1-(1-Ethoxycarbonyl-4-piperidinyl)-4-(4-fluorophenyl)-5-(2-(amino)-4-pyrimdinyl)imidazole:

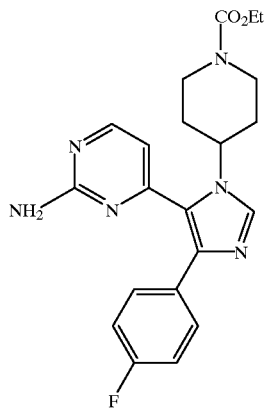

To a solution of the ketoimidazole prepared in Example 2 above (2.6 g, 7.24 mmol) in 15 mL of DMF was added N,N-dimethylformamide dimethyl acetal (1.92 mL, 1.72 g, 14.5 mmol) and the solution was heated at 120° C. for 2 h. At this time, TLC and HPLC indicated no starting material and the solution was cooled to 95° C. and ethanol (30 mL), guanidine•HCl (2.77 g, 28.95 mmol) and $K_2CO_3$ (4.0 g, 28.9 mmol) were added. After 16 hours, HPLC indicated that the reaction was complete and the solution was cooled to room temperature. The solution was diluted with 100 mL of EtOAc and washed with 2×150 mL of 3N HCl. The aqueous layers were combined and basified with excess solid $K_2CO_3$ until the bubbling ceased. The aqueous layer was transferred to a separatory funnel and extracted 2×150 mL of EtOAc. The combined organics were dried over $Na_2SO_4$ and activated charcoal, filtered through Celite, and concentrated in vacuo. The residue was recrystallized from EtOAc/MeOH/Hexanes to yield the imidazole product (0.9 g, 30%) as a beige solid: mp=228–230° C.; IR (KBr) 3321, 3157, 1712, 1658, 1568, 1507, 1470, 1437 cm$^{-1}$; $^1$H NMR (CDCl$_3$) δ8.17 (1H, d, J=5.3 Hz), 7.71 (1H, s), 7.43 (2H, m), 7.00 (2H, t, J=8.7 Hz), 6.50 (1H, d, J=5.3 Hz), 5.16 (2H, br s), 4.74 (1H, tt, J=3.7, 12.0 Hz), 4.35 (2H, m), 4.15 (2H, q, J=7.1 Hz), 2.82 (2H, t, J=12.5 Hz), 2.15 (2H, d, J=12.5 Hz), 1.85 (2H, m), 1.28 (3H, t, J=7.1 Hz); $^{13}$C NMR (DMSO-d$_6$) δ163.61, 162.76, 159.54, 158.66, 158.01, 154.35, 138.88, 136.25, 131.00, 129.16, 129.05, 124.98, 115.08, 114.80, 110.84, 60.64, 53.06, 42.70, 32.48, 14.43; Anal. Calcd for $C_{21}H_{23}N_6O_2F$; C, 61.4; H, 5.7; N, 20.5; Found C, 61.0, H, 5.5; N, 20.3.

Examples 5 (a) to (d) include the alternative conditions

| Solvent | DMFDMA temp | Base | Pyrimidine temp. |
|---------|-------------|------|------------------|
| EtOH    | 90 ° C.     | NaOMe | 80° C.          |
| EtOH    | 90 ° C.     | NaOMe | 85° C.          |
| DMF     | 120 ° C.    | $K_2CO_3$/EtOH | 95° C.   |
| Toluene | 115 ° C.    | $K_2CO_3$/EtOH/IPA | 80–90 ° C. |

EXAMPLE 6

1-(4-piperidinyl)-4-(4-fluorophenyl)-5-[2-(amino)-4-pyrimdinyl]imidazole

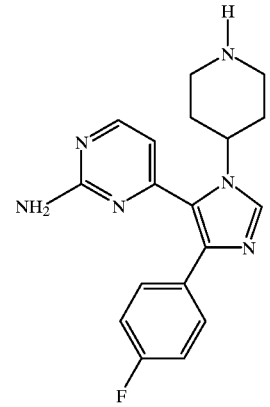

To a solution of the ketoimidazole prepared in Example 2 above (1.4 g, 3.89 mmol) in 5 mL of toluene was added N,N-dimethylformamide dimethyl acetal (1.04 mL, 0.93 g, 7.80 mmol) and the solution was heated at 115° C. for 4 h. At this time, TLC and HPLC indicated no starting material and the solution was cooled to 80 ° C. and 2-propanol (25 mL), guanidine•HCl (1.49 g, 15.6 mmol) and $K_2CO_3$ (2.15 g, 15.6 mmol) were added. After 16.5 hours, HPLC indicated that the reaction was 60% complete. Ethanol (20 mL) was added and heating was continued at 90° C. for 24 h, at which point HPLC showed none of the aminoenone remaining. AT this point, KOH (2.19 g, 38.9 mmol) and water (10 mL) were added and heating was continued at 95° C. for 8 h. An additional poriton of KOH (2.2 g, 38.9 mmol) was added. After 15 h of heating an additional 4.4 g of KOH was added and heated for 48 h. The solution was cooled to room temperature, diluted with 20 mL of water and the solid which formed was filtered, washed with water (50 mL) and Et$_2$O (50 mL), and dried to yield 0.44 g (34%) of the title compound as a beige solid: mp=199–200° C.; IR (KBr) 3471, 3395, 3314, 3167, 1635, 1576, 1566, 1507, 1460 cm$^{-1}$; $^1$H NMR (DMSO-d$_6$) δ 8.20 (1H, d, J=5.0 Hz), 7.98 (1H, s), 7.43 (2H, m), 7.12 (2H, t, J=8.9 Hz), 6.81 (2H, br s), 6.41 (1H, d, J=5.0 Hz), 4.31 (1H, m), 2.97 (2H, d, J=12.4 Hz), 2.45 (2H, m), 1.86 (2H, m), 1.74 (2H, dq, J=3.7, 11.8 Hz); $^{13}$C NMR (DMSO-d$_6$) δ163.67, 162.70, 159.47, 158.68, 158.33, 138.64, 135.79, 130.98, 128.98, 128.88, 125.05, 115.05, 114.77, 110.96, 53.84, 45.39, 34.08; Anal. Calcd for C$_{18}$H$_{19}$N$_6$F•0.5 H$_2$O: C, 62.2; H, 5.8; N, 24.2. Found C, 61.9; H, 5.7; N, 23.9.

In an alternative procedure, the substrate was dissolved in 1-PrOH and heated at about 95° C. with DMFDMA, then heated with guanidine•HCl and K$_2$CO$_3$ at 95° C. and when the pyridine formation was completed, the reaction was heated with excess KOH until product formation was complete.

EXAMPLE 7

2,2,6,6-Tetramethyl-4-(2-oxopropylidene) aminopiperidine

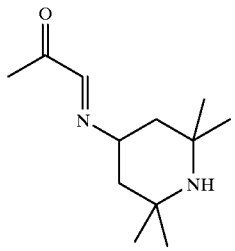

To a solution of pyruvaldehyde (40% w/w solution in water, 2.68 mL, 3.16 g, 17.5 mol) in 30 ml of TBME at room temperature was added dropwise 2,2,6,6-tetramethyl-4-amino-piperidine (2.0 mL, 2.19 g, 14.0 mmol). After 30 min, the solution was diluted with 50 mL of TBME and washed with 3×25 mL of water and 25 mL of brine. The solution was concentrated in vacuo to yield 2.1 g (71%) of the imine product which was used as such in the subsequent step: $^1$H NMR (CDCl$_3$) δ7.64 (1H, s), 3.70 (1H, tt, J=3.9, 11.6 Hz), 2.34 (3H, s), 1.61 (2H, dd, J=3.9, 13.0 Hz), 1.32 (2H, t, J=12.2 Hz), 1.21 (6H, s), 1.14 (6H, s).

EXAMPLE 8

1-(2,2,6,6-tetramethyl-4-piperidinyl)-4-(4-fluorophenyl)-5-acetylimidazole:

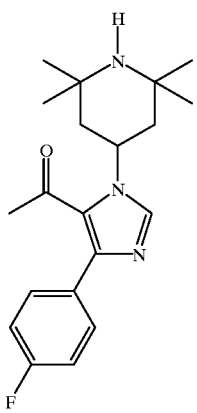

a solution of pyruvaldehyde (40% w/w solution in water, 7.56 mL, 8.91 g, 49.5 mmol) in 90 mL of DMSO at room temperature was added dropwise 2,2,6,6-tetramethyl-4-amino-piperidine (9.24 mL, 8.43 g, 65.4 mmol). After 10 min α-(p-toluenesulfonyl)-4-fluorobenzylisonitile (13.0 g, 44.95 mmol) and K$_2$CO$_3$ (7.46 g, 53.95 mmol) were added. After 23 h, the solution was diluted with 250 mL of EtOAc and washed with 2×200 mL of 3N HCl. The aqueous layers were combined and basified with excess solid K$_2$CO$_3$ until the bubbling ceased. The aqueous layer was transferred to a separatory funnel and extracted 2×250 mL of EtOAc. The combined organics were washed with 3×100 mL of water and concentrated in vacuo to yield the title compound (11.6 g, 75%) as a brown oil, which could be recrystallized from CHCl$_3$/hexanes: mp=134–36° C.; IR (KBR) 3430, 3144, 1659, 1653, 1219 cm$^{-1}$; $^1$H NMR (CDCl$_3$) δ7.76 (1H, s), 7.43 (2H, m), 7.12 (2H, t, J=8.7 Hz), 5.39 (1H, tt, J=3.1, 12.5 Hz), 2.11 (3H, s), 2.10 (2H, m), 1.50 (2H, t, J=12.2 Hz), 1.37 (6H, s), 1.22 (6H, s); $^{13}$C NMR (CDCl$_3$) δ190.77, 164.69, 161.41, 149.79, 137.42, 131.47, 131.36, 127.03, 115.57, 115.29, 52.02, 50.57, 46.20, 34.61, 30.45, 28.06.

Alternative reaction conditions for this synthesis included

| Solvent | Base eq. | Imine formation temp | Cycloaddition temp. | Imine formation time |
|---|---|---|---|---|
| DMF | K$_2$CO$_3$/1.25 | room temp. | room temp. | 15 min. |
| DMF/toluene | K$_2$CO$_3$/1.15 | room temp to 65° C. (-H$_2$O) | room temp. | 80 min. |

-continued

| Solvent | Base eq. | Imine formation temp | Cycloaddition temp. | Imine formation time |
|---|---|---|---|---|
| DMF | none | room temp. | room temp. | 15 min. |
| DMF/EtOAc | $K_2CO_3$/1.2 | room temp. | room temp. | 15 min. |
| DMSO | $K_2CO_3$/1.25 | room temp. | room temp. | 20 min. |
| DMSO/toluene | $K_2CO_3$/1.15 | room temp to 55° C. (—$H_2O$) | room temp. | 35 min. |
| DMSO/ (MeO)$_3$CH | $K_2CO_3$/1.2 | room temp to 55° C. (—$H_2O$) | room temp. | 40 min. |
| DMSO | morpholine/1.3 | room temp. | room temp. | 15 min. |
| DMSO | pyrrolidine/1.3 | room temp. | room temp. | 15 min. |
| DMSO | $K_3PO_4$/1.5 | room temp. | room temp. | 15 min. |
| DMSO | $K_2HPO_4$/1.5 | room temp. | room temp. | 15 min. |
| DMSO | DBU/1.1 | room temp. | room temp. | 15 min. |
| DMSO | $Na_2CO_3$/1.2 | room temp. | room temp. | 15 min. |
| DMSO | $Na_2HPO_4$/1.5 | room temp. | room temp. | 15 min. |
| DMSO | $K_2HPO_4$/3.0 | room temp. | room temp. | 15 min. |
| DMSO | morpholine/1.05 | room temp. | room temp. | 18 min. |
| DMSO | morpholine/1.0 | room temp. | room temp. | 10 min. |
| EtOAc | morpholine/1.0 | room temp. | room temp. | 10 min. |
| EtOAc | $K_2CO_3$/1.0 | room temp | room temp. | 12 min. |
| EtOAc | $K_2CO_3$/1.0 | room temp | 50° C. | 13 min. |
| EtOAc | $K_2CO_3$/1.0 | room temp | 35° C. | 15 min. |
| EtOAc | $K_2CO_3$/1.0 | room temp | 40° C. | 15 min. |

EXAMPLE 9

1-(2,2,6,6-tetramethyl-4-piperidinyl)-4-(4-fluorophenyl)-5-(3-N,N-dimethylamino-trans-1-propenone)imidazole

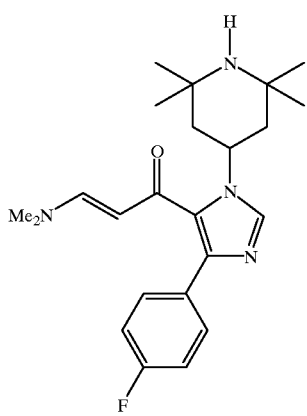

The ketoimidazole prepared in Example 8 above (0.75 g, 2.18 mmol) was dissolved in 10 mL of toluene and N,N-dimethylformamide diethyl acetal (0.43 mL, 0.39 g, 3.28 mmol) and was heated at 115° C. for 20 h. The solution was cooled to room temperature and the solvents were removed under vacuum. The residue was passed through a short plug of silica gel and eluted with EtOAc/MeOH (1:1), and concentrated to give the title compound (0.65 g 76%) of the title compound as a brown solid: $^1$H NMR (CDCl$_3$) δ7.65 (1H, s), 7.56 (2H, m), 7.46 (1H, d, J=12.2 Hz), 7.01 (2H, t, J=8.8 Hz), 5.32 (1H, m), 5.01 (1H, d, J=12.6 Hz), 2.96 (3H, br s), 2.48 (3H, br s), 2.09 (2H, dd, J=3.1, 12.0 Hz), 1.44 (2H, t, J=12.3 Hz 1.31 (6H, s), 1.17 (6H, s).

EXAMPLE 10

1-(2,2,6,6-tetramethyl-4-piperidinyl)-4-(4-fluorophenyl)-5-[2-(methylamino)-4-pyrimidinyl]imidazole

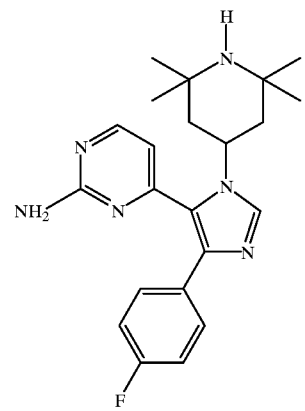

To a solution of the ketoimidazole prepared in Example 8 above (8.0 g, 23.3 mmol) in 100 mL of DMSO was added N,N-dimethylformamide dimethyl acetal (6.19 mL, 5.55 g, 46.6 mol) and the solution was heated at 100° C. for 16 h. At this time, HPLC indicated no starting material and guandine•HCl (4.45 g, 46.6 mmol) and $K_2CO_3$ (6.44 g, 46.6 mmol) were added and heating was continued at 100° C. After 9 hours, the solution was cooled to room temperature, diluted with 100 mL of water, DMSO and MeOH, and filtered. The filtrate was diluted with 200 mL of EtOAc and 400 mL of water. The layers were separated and the aqueous layer was extracted 3×200 mL of EtOAc. The organic layers were combined and washed with 3×100 mL of water. The organics were washed with 50 mL of brine, dried over $Na_2SO_4$ and activated charcoal, concentrated and the residue was recrystallized from EtOAc/hexanes to give 3.3 g (36%)

of the title compound: m=221–22° C.; IR (KBr) 3345, 3319, 3155, 1645, 1562 cm$^{-1}$; $^1$H NMR (CDCl$_3$) δ8.17 (1H, d, J=5.1 Hz), 7.72 (1H, s), 7.45 (2H, m), 7.00 (2H, t, J=8.7 Hz), 6.49 (1H, d, J=5.2 Hz), 5.30 (1H, tt, J=3.2, 12.6 Hz), 5.12 (2H, br s), 2.04 (2H, dd, J=3.2, 12.4 Hz), 1.48 (2H, t, J=12.3 Hz), 1.24 (6H, s), 1.17 (6H, s); $^{13}$C NMR (DMSO-d$_6$) δ163.67, 162.72, 159.49, 158.77, 158.49, 138.68, 135.43, 130.92, 128.93, 128.82, 125.14, 115.09, 114.81, 111.00, 50.81, 48.67, 44.74, 34.06, 28.11. Anal. Calcd for C$_{22}$H$_{27}$N$_6$F: C, 66.98; H, 6.90; N, 21.30. Found C, 67.37; H, 6.88; N, 21.39.

Alternative conditions employed include

| Solvent | DMFDMA temp | Base | Pyrimidine temp. |
|---------|-------------|------|------------------|
| DMF | 100° C. | K$_2$CO$_3$ | 120° C. |
| DMSO | 100° C. | K$_2$CO$_3$ | 100° C. |
| DMSO | 100° C. | KOH | 100° C. |
| 1-PrOH | 100° C. | KOH/H$_2$O | 100° C. |
| EtOH | 85° C. | NaOMe | 85° C. |
| 2-PrOH | 85° C. | NaOMe | 85° C. |

In yet another alternative procedure to those listed above, the title compound was prepared in the following manner: To a solution of pyruvaldehyde (40% w/w solution in water, 5.82 mLL, 6.85 g, 38.04 mmol) in 70 mL of DMSO at room temperature was added 2,2,6,6-tetramethyl-4-aminopiperidine (6.52 ml, 5.94 g, 38.04 mmol). After 15–20 min, α-(p-toluenesulfonyl)-4-fluorobenzylisonitrile (10 g, 34.6 mmol) and K$_2$CO$_3$ (5.02 g, 36.3 mmol) were added. After 19 h, an HPLC solution assay indicated that 6.79 g (57%) of the ketoimidazole (title compound of Example 8) had formed and that reaction was complete. To the solution was added 30 mL of toluene, and the solution was heated at 65° C. while the toluene was removed under vacuum. The toluene addition/distillation was repeated two times more. N,N-dimethylformamide dimethyl acetal (DMFDMA) (9.2 mL, 8.24 g, 69.2 mmol) was added and the solution was heated at 100° C. After 2 h, HPLC indicated no reaction, so an additional 9.2 mL of DMFDMA were added, and after 15 h an additional 5 mL of DMFDMA were added and heated for 1 h. Guanidine•HCl (6.61 g, 69.2 mmol) and K$_2$CO$_3$ (9.56 g, 69.2 mmol) were added and heated at 100° C. for 6.75 h, at which point HPLC indicated that the reaction was complete. After cooling to room temperature, the solution was filtered through a pad of Celite, diluted with 250 mL of EtOAc and washed with 4×200 mL of 3N HCl. The aqueous layers were combined and basified with solid KOH to pH=14. The aqueous layer was transferred to a separatory funnel and extracted 3×200 mL of EtOAc. The combined organics were washed with 3×100 mL of 3N KOH solution and 50 mL of brine, dried over Na$_2$SO$_4$ and activated charcoal, filtered through Celite and concentrated in vacuo. The residue was dissolved in 50 mL of MeOH and the crystals which formed were filtered and washed with 100 ml of EtOAc to yield the title compound (4.89 g, 36%) as a tan solid.

EXAMPLE 11

1-(1-t-Butoxycarbonyl-4-piperidinyl)-4-(4-fluorophenyl)-5-acetylimidazole

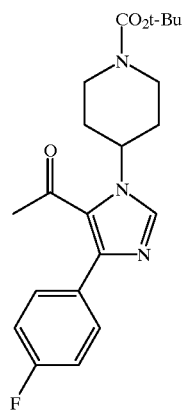

To a solution of t-butyl 4-amino-piperidinecarboxylate (0.95 g, 4.75 mmol) in 40 mL of Et$_2$O was added pyruvaldehyde (40% w/w solution in water, 0.94 mL, 1.11 g, 6.17 mmol) at room temperature. After 1.75 h, the solution was poured into a separatory funnel, diluted with 30 mL of Et$_2$O and 10 mL of EtOAc, and washed with 2×10 mL of water. The organics were concentrated in vacuo and the residue was diluted in 10 mL of DMF and α-(p-toluenesulfonyl)-4-fluoro-benzylisonitrile (1.37 g, 4.75 mmol) and K$_2$CO$_3$ (0.72 g, 5.23 mmol) were added. After 16 h, the solution was diluted with 100 mL of water and extracted with 2×40 mL of EtOAc. The combined organics were washed with 3×40 mL of 10% HCl. The aqueous layers were combined and neutralized with excess solid NaHCO$_3$, then basified with 20 mL of 10% KOH. The aqueous layer was transferred to a separatory funnel and extracted 3×30 mL of EtOAc. The combined organics concentrated in vacuo to yield the imidazole product (0.5 g, 27%): $^1$H NMR (CDCl$_3$) δ7.74, 7.44 (2H, m), 7.13 (2H, t, J=8.6 Hz), 4.97 (1H, tt, J=3.7, 12.0 Hz), 4.29 (2H, m), 2.88 (2H, m), 2.15 (2H, m) 2.11 (3H, s), 1.78 (2H, dq, 4.2, 12.2 Hz), 1.48 (9H, s).

EXAMPLE 12

1-Benzyl-4-(2-oxopropylidene)aminopiperidine

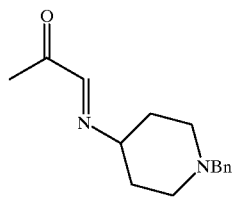

To a solution of pyruvaldehyde (40% w/w solution in water, 0.49 mL, 0.57 g, 3.19 mmol) in 10 mL of Et$_2$O at room temperature was added dropwise 4-amino-1-benzylpiperidine (0.5 mL, 0.46 g, 2.45 mmol). After 20 min, the solution was diluted with 40 mL of Et$_2$O and washed with 2×5 mL of water. The solution was concentrated in vacuo to yield the imine product which was used as such in the subsequent step: $^1$H NMR (CDCl$_3$) δ7.62 (1H, s), 7.29 (5H, m), 3.53 (2H, s), 3.28 (1H, m), 2.91 (2H, m), 2.38 (3H, s), 2.15 (2H, m), 1.84 (2H, m), 1.69 (2H, m)

EXAMPLE 13

1-(1-Benzyl-4-piperidinyl)-4-(4-fluorophenyl)-5-acetylimidazole

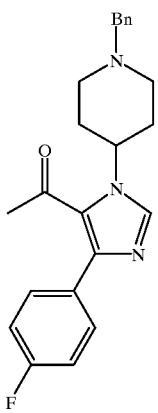

To a solution of the inline described in Example 12 above (assumed 100% yield for Example 12, 0.64 g, 2.44 mmol) in 5 mL of DMF at 0° C. was added α-(p-toluenesulfonyl)-4-fluorobenzylisonitrile (0.85 g, 2.93 mmol) and K$_2$CO$_3$ (0.40 g, 2.93 mmol) and K$_2$CO$_3$ (0.40 g, 2.93 mmol). The solution was stirred at 0° C. for 2 h, then gradually warmed to room temperature over 15 h. The solution was diluted with 70 mL of EtOAc and washed with 100 and 50 mL of water. The organic layer was acidified with 2×55 mL of 3N HCl. The aqueous layers were combined and neutralized with solid NaHCO$_3$ then basified with 30 mL of 10% KOH. The aqueous layer was transferred to a separatory funnel, extracted with 2×50 mL of EtOAc and concentrated in vacuo to yield the title compound (0.38 g, 41%) which was used in subsequent steps: $^1$H NMR (CDCl$_3$) δ7.78 (1H, s), 7.43 (2H, m), 7.27 (5H, m), 7.11 (2H, t, J=8.6 Hz), 4.80 (1H, tt, J=3.9, 11.8 Hz), 3.55 (2H, s), 3.02 (2H, d, J=11.9 Hz), 2.16 (2H, m), 2.10 (3H, s), 1.94 (2H, m).

EXAMPLE 14

1-(1-Benzyl-4-piperidinyl)-4-(4-fluorophenyl)-5-[2-(amino)-4-pyrimidinyl]imidazole

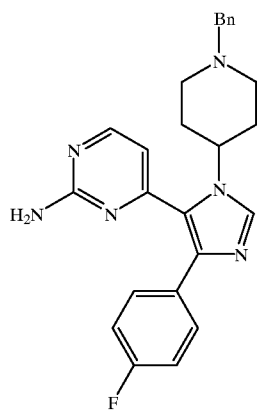

To a solution of the ketoimidazole prepared in Example 13 above (0.38 g, 1.01 mmol) in 5 mL of EtOH was added N,N-dimethylformamide dimethyl acetal (0.4 mL, 0.36 g, 3.02 mmol) and the solution was heated at 90° C. for 3 h. After 3 h, an additional 1 mL of DMFDMA was added and heated for 3 h. At this time, TLC indicated no starting material and the solution was cooled to 70° C. and guanidine•HCl (0.19 g, 2.02 mmol) and NaOMe (25% w/w solution, 0.46 mL, 0.44 g, 2.02 mmol) were added. After 15 hours, additional N-methylguanidine•HCl (0.19 g, 2.02 mmol) and NaOMe (25% w/w solution, 0.46 mL, 0.44 g, 2.02 mmol) were added and heated at 75° C. for 24 h. The solution was cooled to room temperature, diluted with 50 mL of water and extracted 2×50 mL of EtOAC. The combined organics were concentrated and the residue was recrystallized from EtOAc to give 0.2 g (47%) of the title compound: $^1$H NMR (CDCl$_3$) δ8.19 (1H, d, J=5.2 Hz), 7.76 (1H, s), 7.44 (2H, m), 7.33 (5H, m), 7.01 (2H, t J=8.6 Hz), 6.50 (1H, d, J=5.2 Hz), 5.17 (2H, br s), 4.54 (1H, m), 3.53 (2H, s), 3.02 (2H, m), 2.09 (6H, m).

Additional compounds produced using the analogous methods to those indicated above include Example 15: 5-(2-Phenylamino-4-pyrimdinyl)-4-(4-fluorophenyl)-1-(4-piperidinyl)imidazole Example 16: 1-[1-Carbomethoxy)piperidin-4-yl]-4-(4-fluorophenyl)-5-[[2-[3-benzylo)phenylamino]pyrimidin-4-]imidazole Example 17: 1-[1-Carbomethoxy)piperidin-4-yl]-4-(4-fluorophenyl)-5-[[2-[4-benzylox)phenylamino]pyrimdin-4-yl]]imidazole Example 18: 1-(Piperdin-4-yl)-4-(4-fluorophenyl)-5-[2-(3-tifluoromethylphenyl)-amino]pyrimidin-4-yl)imidazole Example 19: 1-(Piperdin-4-yl)-4-(4-fluorophenyl)-5-[2-(3-4,difluorophenyl)-amino]pyrimidin-4-yl)imidazole The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound of the formula:

(VIII)

wherein $R_b$ is an alkyl, aryl, heteroaryl, cycloalkyl, cycloalkenyl, arylalkyl, heteroarylalkyl, heterocyclic, or heterocyclicalkyl, all of which are unsubstituted or substituted;

R is unsubstituted or substituted alkyl, unsubstituted or substituted aryl, halogen, hydroxyl, thiol, $C_{1-10}$ alkoxy, $C_{1-10}$ alkylthio, $C_{1-10}$ alkylsulfinyl, $CH_2OR_{12}$, amino, mono or di-$C_{1-10}$ alkyl substituted amino, $NHR_{21}$, $N(R_{10})C(O)R_a$ or an N-heterocyclyl ring which ring has from 5 to 7 members and does not contain or contains an additional heteroatom selected from oxygen, sulfur or $NR_{15}$;

$R_a$ is hydrogen, $C_{1-6}$ alkyl, $C_{3-7}$ cycloalkyl, aryl, arylC$_{1-4}$ alkyl, heteroaryl, heteroarylC$_{1-4}$alkyl, heterocyclyl, or heterocyclylC$_{1-4}$ alkyl;

$R_4$ is an unsubstituted or substituted phenyl, naphth-1-yl or naphth-2-yl, or heteroaryl ring;

$R_2$ is -$(CR_{10}R_{20})_n\prime OR_9$, heterocyclyl, heterocyclylC$_{1-10}$ alkyl, $C_{1-10}$alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkylC$_{1-10}$ alkyl, $C_{5-7}$ cycloalkenyl, $C_{5-7}$cycloalkenyl-C$_{1-10}$-alkyl, aryl, arylC$_{1-10}$ alkyl, heteroaryl, heteroaryl-C$_{1-10}$ -alkyl, $(CR_{10}R_{20})_nOR_{11}$, $(CR_{10}R_{20})_nS(O)_mR_{18}$, $(CR_{10}R_{20})_n$NHS $(O)_2R_{18}$, $(CR_{10}R_{20})_nNR_{13}R_{14}$, $(CR_{10}R_{20})_nNO_2$, $(CR_{10}R_{20})_nCN$, $(CR_{10}R_{20})_n\prime SO_2R_{18}$, $(CR_{10}R_{20})_nS(O)_{m\prime}NR_{13}R_{14}$, $(CR_{10}R_{20})_nC(Z)R_{11}$, $(CR_{10}R_{20})_nOC(Z)R_{11}$, $(CR_{10}R_{20})_nC(Z)OR_{11}$, $(CR_{10}R_{20})_nC(Z)NR_{13}R_{14}$, $(CR_{10}R_{20})_nC(Z)NR_{11}OR_9$, $(CR_{10}R_{20})_nNR_{10}C(Z)R_{11}$, $(CR_{10}R_{20})_nNR_{10}C(Z)NR_{13}R_{14}$, $(CR_{10}R_{20})_nN(OR_6)C(Z)NR_{13}R_{14}$, $(CR_{10}R_{20})_nN(OR_6)C(Z)R_{11}$, $(CR_{10}R_{20})_nC(=NOR_6)R_{11}$, $(CR_{10}R_{20})_nNR_{10}C(=NR_{19})NR_{13}R_{14}$, $(CR_{10}R_{20})_nOC(Z)NR_{13}R_{14}$, $(CR_{10}R_{20})_nNR_{10}C(Z)NR_{13}R_{14}$, $(CR_{10}R_{20})_nNR_{10}$, $C(Z)OR_{10}$, 5-$(R_{18})$-1,2,4-oxadizaol-3-yl or 4-$(R_{12})$-5-$R_{18}R_{19}$)-4,5-dihydro-1,2,4-oxadiazol-3-yl; wherein the aryl, arylalkyl, heteroaryl, heteroaryl alkyl, heterocyclic and heterocyclic alkyl may be unsubstituted or substituted;

n is an integer having a value of 1 to 10;

n' is 0, or an integer having a value of 1 to 10;

m is 0, or the integer 1 or 2;

m' is an integer having a value of 1 or 2;

Z is oxygen or sulfur;

$R_6$ is hydrogen, a pharmaceutically acceptable cation, $C_{1-10}$ alkyl, $C_{3-7}$ cycloalkyl, aryl, arylC$_{1-4}$ alkyl, heteroaryl, heteroarylalkyl, heterocyclyl, aroyl, or $C_{1-10}$ alkanoyl;

$R_9$ is hydrogen, $C(Z)R_{11}$ or unsubstituted or substituted $C_{1-10}$ alkyl, $S(O)_2R_{18}$, unsubstituted or substituted aryl or unsubstituted or substituted aryl-C$_{1-4}$ alkyl;

$R_{10}$ and $R_{20}$ is each independently selected from hydrogen or $C_{1-4}$ alkyl;

$R_{11}$ is hydrogen, $C_{1-10}$ alkyl, $C_{3-7}$ cycloalkyl, heterocyclyl, heterocyclyl $C_{1-10}$alkyl, aryl, arylC$_{1-10}$ alkyl, heteroaryl or heteroarylC$_{1-10}$ alkyl;

$R_{12}$ is hydrogen or $R_{16}$;

$R_{13}$ and $R_{14}$ is each independently selected from hydrogen or unsubstituted or substituted $C_{1-4}$ alkyl, unsubstituted or substituted aryl or unsubstituted or substituted aryl-C$_{1-4}$ alkyl, or together with the nitrogen to which they are attached form a heterocyclic ring of 5 to 7 members which ring does not contain or contains an additional heteroatom selected from oxygen, sulfur or $NR_9$;

$R_{15}$ is $R_{10}$ or $C(Z)$-$C_{1-4}$ alkyl;

$R_{16}$ is $C_{1-4}$ alkyl, halo-substituted-$C_{1-4}$ alkyl, or $C_{3-7}$ cycloalkyl;

$R_{18}$ is $C_{1-10}$ alkyl, $C_{3-7}$ cycloalkyl, heterocyclyl, aryl, arylalkyl, heterocyclyl, heterocyclyl-C$_{1-10}$alkyl, heteroaryl or heteroarylalkyl;

$R_{19}$ is hydrogen, cyano, $C_{1-4}$ alkyl, $C_{3-7}$ cycloalkyl or aryl;

$R_{21}$ is an alkyl, aryl, arylC$_{1-6}$alkyl, heterocyclic, heterocyclylC$_{1-6}$ alkyl, heteroaryl, or heteroarylC$_{1-6}$alkyl moiety, wherein each of these moieties may be unsubstituted or substituted.

2. The compound according to claim 1 wherein $R_4$ is 4-fluorophenyl, and $R_2$ is an unsubstituted or substituted heterocyclic, $C_{1-10}$ alkyl, $C_{3-7}$ cycloalkyl, or $C_{3-7}$ cycloalkyl $C_{1-10}$ alkyl.

3. The compound according to claim 2 wherein R is $C_{1-4}$ alkoxy, $C_{1-4}$ alkyl thio, or amino.

4. The compound according to claim 2 wherein $R_2$ is an unsubstituted or substituted heterocyclic.

5. The compound according to claim 4 wherein the heterocyclic is a piperidin-4-yl.

6. The compound 1 according to claim 5 wherein the piperidin-4-yl ring is a 1-ethoxy carbonyl-4-piperidinyl, 1-t-butoxycarboxy-4-piperidinyl, or 1-benzyl-4-piperidinyl.

* * * * *